United States Patent
Davis et al.

(10) Patent No.: US 10,744,317 B2
(45) Date of Patent: Aug. 18, 2020

(54) ENTERAL ADAPTOR COUPLINGS

(71) Applicant: NEOMED, INC., Woodstock, GA (US)

(72) Inventors: Benjamin M. Davis, Woodstock, GA (US); Aaron N. Ingram, Canton, GA (US); Mark M. Costello, County Mayo (IE); John Burke, County Roscommon (IE)

(73) Assignee: NeoMed, Inc., Woodstock, GA (US)

( * ) Notice: Subject to any disclaimer, the term of this patent is extended or adjusted under 35 U.S.C. 154(b) by 457 days.

(21) Appl. No.: 15/211,585

(22) Filed: Jul. 15, 2016

(65) Prior Publication Data
US 2017/0014616 A1  Jan. 19, 2017

Related U.S. Application Data

(60) Provisional application No. 62/207,123, filed on Aug. 19, 2015, provisional application No. 62/192,759, filed on Jul. 15, 2015.

(51) Int. Cl.
| | | |
|---|---|---|
| *A61M 39/10* | (2006.01) | |
| *A61M 39/22* | (2006.01) | |
| *A61J 15/00* | (2006.01) | |
| *A61M 31/00* | (2006.01) | |

(52) U.S. Cl.
CPC .......... *A61M 39/22* (2013.01); *A61J 15/0076* (2015.05); *A61M 31/00* (2013.01); *A61M 39/10* (2013.01); *A61M 2039/1033* (2013.01); *A61M 2039/1038* (2013.01); *A61M 2039/1077* (2013.01)

(58) Field of Classification Search
CPC .. A61M 39/10; A61M 39/22; A61M 39/1033; A61M 39/1077; A61M 2039/1027; A61M 2039/1033; A61M 2039/1072; A61M 2039/1077
See application file for complete search history.

(56) References Cited

U.S. PATENT DOCUMENTS

| | | |
|---|---|---|
| 3,572,337 A | 3/1971 | Schunk |
| 3,751,077 A | 8/1973 | Hiszpanski |
| 4,390,017 A | 6/1983 | Harrison |
| (Continued) | | |

FOREIGN PATENT DOCUMENTS

| | | |
|---|---|---|
| DE | 20302788 U1 | 6/2004 |
| EP | 0960616 A2 | 12/1999 |
| (Continued) | | |

OTHER PUBLICATIONS

ISO 594:2: 1998 (E). p. 8. (Year: 1998).*
(Continued)

*Primary Examiner* — Nathan R Price
*Assistant Examiner* — Melissa A Snyder
(74) *Attorney, Agent, or Firm* — Dority & Manning, P.A.

(57) ABSTRACT

An enteral adapter coupling for connecting non-ENFit threaded enteral equipment with ISO 80369-3 compliant and compatible enteral equipment. The adapter coupling includes a first end substantially corresponding to an ISO 80369-3 coupling format, a second end substantially conforming to a threaded enteral feeding coupling format, and an internal lumen extending through the coupling allowing fluid communication between the first end and the second end.

20 Claims, 13 Drawing Sheets

(56) References Cited

U.S. PATENT DOCUMENTS

| | | |
|---|---|---|
| 4,685,173 A | 8/1987 | Pavur |
| D303,710 S | 9/1989 | Neill |
| 5,047,021 A | 9/1991 | Utterberg |
| D327,318 S | 6/1992 | Dudar et al. |
| 5,176,415 A | 1/1993 | Choksi |
| 5,218,965 A | 6/1993 | Ring |
| 5,535,771 A | 7/1996 | Purdy |
| 5,697,918 A | 12/1997 | Fischer |
| D395,502 S | 6/1998 | Deily et al. |
| D398,060 S | 9/1998 | Brown |
| 5,921,965 A | 7/1999 | Beli |
| D435,652 S | 12/2000 | Nazarifar et al. |
| 6,267,154 B1 | 7/2001 | Felicelli |
| 6,270,519 B1 | 8/2001 | Botts |
| D473,647 S | 4/2003 | Francavilla et al. |
| D534,796 S | 1/2007 | Falkenburg |
| 7,240,926 B2 | 7/2007 | Dalle |
| 7,503,905 B2 | 3/2009 | Jessop et al. |
| 7,666,170 B2 | 2/2010 | Guala |
| 7,799,009 B2 | 9/2010 | Niedospial, Jr. et al. |
| 7,857,284 B2 | 12/2010 | Kimball et al. |
| 7,985,205 B2 | 7/2011 | Adams |
| D644,618 S | 9/2011 | Morihira |
| 8,016,795 B2 | 9/2011 | Barrelle et al. |
| 8,109,902 B2 | 2/2012 | Middleton et al. |
| 8,152,790 B2 | 4/2012 | Lopez et al. |
| 8,303,571 B2 | 11/2012 | Kraushaar et al. |
| 8,398,607 B2 | 3/2013 | Fangrow, Jr. |
| 8,479,370 B2 | 7/2013 | Grant |
| 8,529,524 B2 | 9/2013 | Newton et al. |
| D691,261 S | 10/2013 | Kawamura |
| 8,641,685 B2 | 2/2014 | Mansour et al. |
| 8,679,090 B2 | 3/2014 | Anderson et al. |
| D712,025 S | 8/2014 | Kawamura |
| D714,935 S | 10/2014 | Nishioka et al. |
| D716,636 S | 11/2014 | McDonald |
| D717,948 S | 11/2014 | Strong et al. |
| 9,017,295 B2 | 4/2015 | Pan |
| D731,065 S | 6/2015 | Winter |
| D736,914 S | 8/2015 | Schultz |
| D736,915 S | 8/2015 | Schultz |
| D737,962 S | 9/2015 | Schultz |
| 9,149,623 B1 | 10/2015 | Colman |
| D756,200 S | 5/2016 | McDonald |
| 9,427,715 B2 | 8/2016 | Palazzolo et al. |
| 9,433,562 B2 | 9/2016 | Ingram et al. |
| 10,001,236 B2 | 6/2018 | Lewis et al. |
| 2002/0017328 A1 | 2/2002 | Loo |
| 2005/0209555 A1 | 9/2005 | Middleton et al. |
| 2006/0217679 A1 | 9/2006 | Hanly et al. |
| 2007/0076401 A1 | 4/2007 | Carrez |
| 2008/0312640 A1 | 12/2008 | Grant |
| 2010/0022951 A1 | 1/2010 | Ferrera et al. |
| 2012/0150129 A1 | 6/2012 | Jin |
| 2013/0090606 A1 | 4/2013 | Shams |
| 2014/0246616 A1 | 9/2014 | Fangrow |
| 2014/0276466 A1 | 9/2014 | Yen et al. |
| 2014/0276651 A1* | 9/2014 | Schultz ............... A61M 39/165 604/535 |
| 2015/0238747 A1* | 8/2015 | Russo ............... A61M 39/1011 604/533 |
| 2016/0001056 A1 | 1/2016 | Nelson et al. |
| 2016/0030293 A1 | 2/2016 | Dorsey et al. |
| 2016/0067147 A1 | 3/2016 | Davis et al. |
| 2016/0067422 A1 | 3/2016 | Davis et al. |
| 2016/0067471 A1 | 3/2016 | Ingram et al. |
| 2016/0143815 A1 | 5/2016 | Koelper et al. |
| 2016/0159635 A1 | 6/2016 | Davis et al. |
| 2016/0206516 A1* | 7/2016 | Kunishige ............... A61J 15/00 |
| 2016/0206845 A1 | 7/2016 | Colman et al. |
| 2016/0296740 A1* | 10/2016 | Adams .................. A61M 39/10 |
| 2016/0317393 A1 | 11/2016 | Davis et al. |
| 2016/0367439 A1 | 12/2016 | Davis et al. |
| 2017/0045170 A1 | 2/2017 | Lewis et al. |
| 2017/0239141 A1 | 8/2017 | Davis et al. |

FOREIGN PATENT DOCUMENTS

| | | |
|---|---|---|
| EP | 2269685 A2 | 1/2011 |
| EP | 3042691 A1 | 7/2016 |
| FR | 2930428 A1 | 10/2009 |
| WO | 9200717 A1 | 1/1992 |
| WO | 9932155 A2 | 7/1999 |
| WO | 2005065767 A2 | 7/2005 |
| WO | 2012024370 A1 | 2/2012 |
| WO | 2013081699 A2 | 6/2013 |
| WO | 2016040126 A1 | 3/2016 |
| WO | 2016089869 A1 | 6/2016 |
| WO | 2018022631 A1 | 2/2018 |

OTHER PUBLICATIONS

Alternative Syringes Low Displacement Option PowerPoint Presention; Presented by Rork Swisher of Covidien; ISO 80369 Series Meeting; Berlin Germany; 11 pgs; Mar. 19, 2014.pgs.

Covidien ENFit Coupling; Mar. 2014; 1 pg.

International Search Report & Written Opinion for PCT/US16/23771; Jun. 27, 2016; 17 pgs.

International Search Report & Written Opinion for PCT/US16/42514; Nov. 10, 2016; 12 pgs.

New ISO Tubing Connector Standards: A Follow-Up to the Sentinel Event Alert Webinar PowerPoint Presention; www.jointcommission.org; 50 pgs; Dec. 3, 2014.

New Tube Feeding Connectors Webinar PowerPoint Presention; www.oley.org; 24 pgs; Jun. 24, 2014.

Specialty Medical Products Coupling (Item Code SMP-SCFF); Apr. 10, 2014; 1 pg.

International Search Report & Written Opinion for PCT/US2017/019021; Sep. 22, 2017; 20 pgs.

Invitation to Pay Additional Fees for PCT/US2017/019021; Jun. 6, 2017; 12 pgs.

Invitation to Pay Additional Fees for PCT/US2018/021856; Jun. 27, 2018; 24 pgs.

* cited by examiner

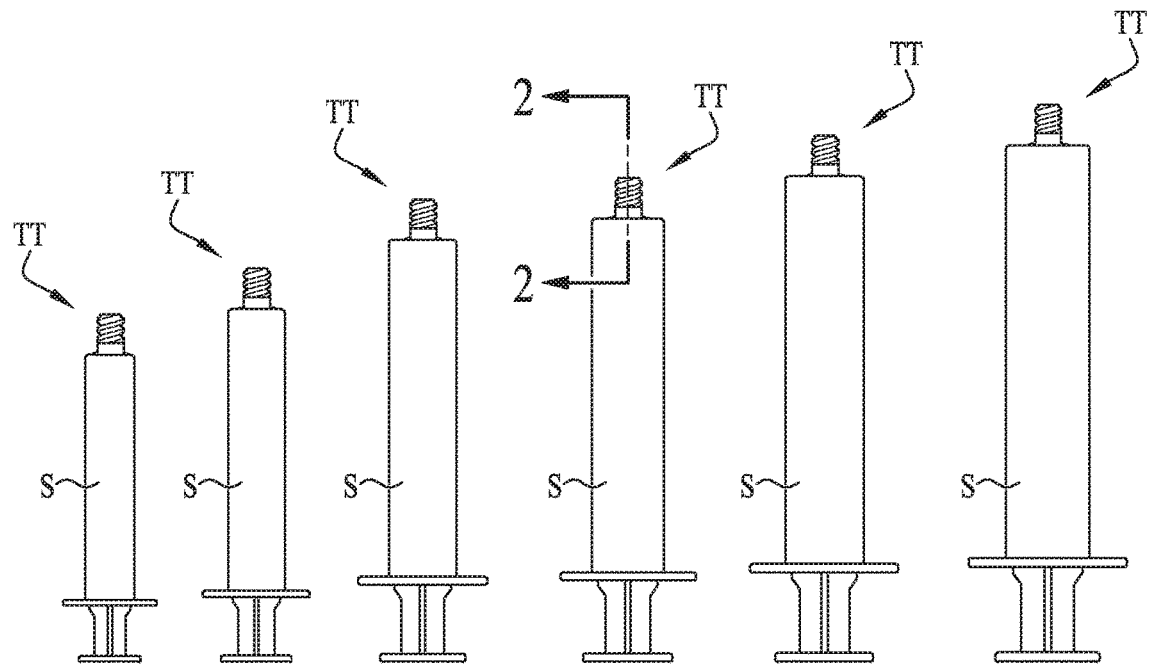
FIG. 1
*PRIOR ART*
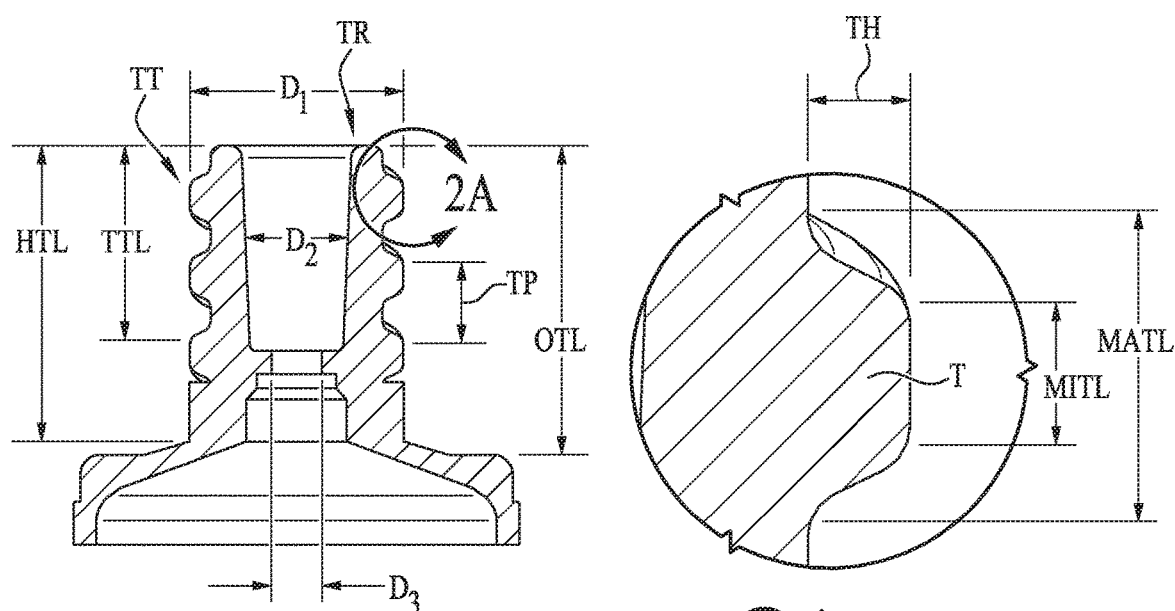
FIG. 2
*PRIOR ART*
FIG. 2A
*PRIOR ART*

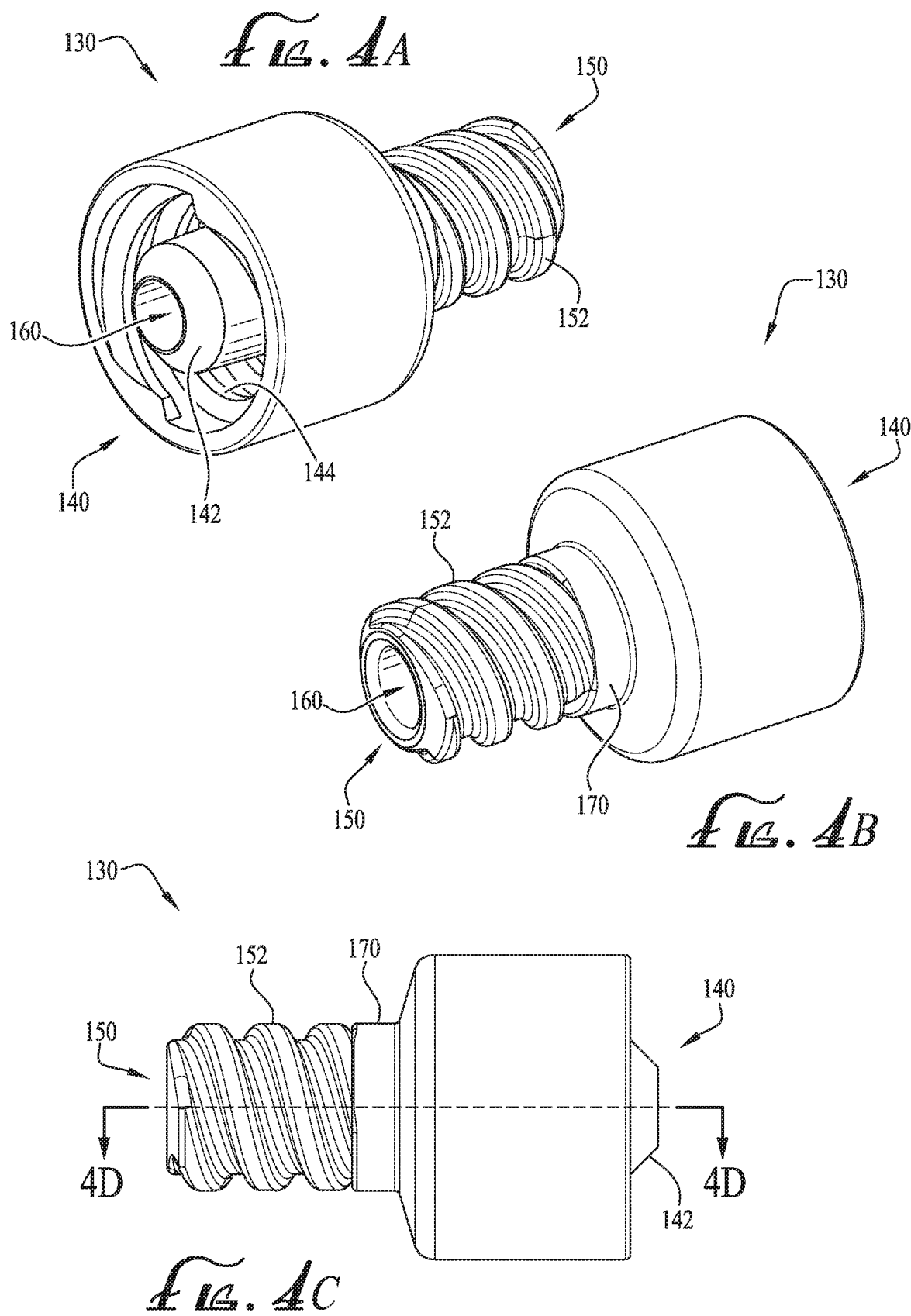

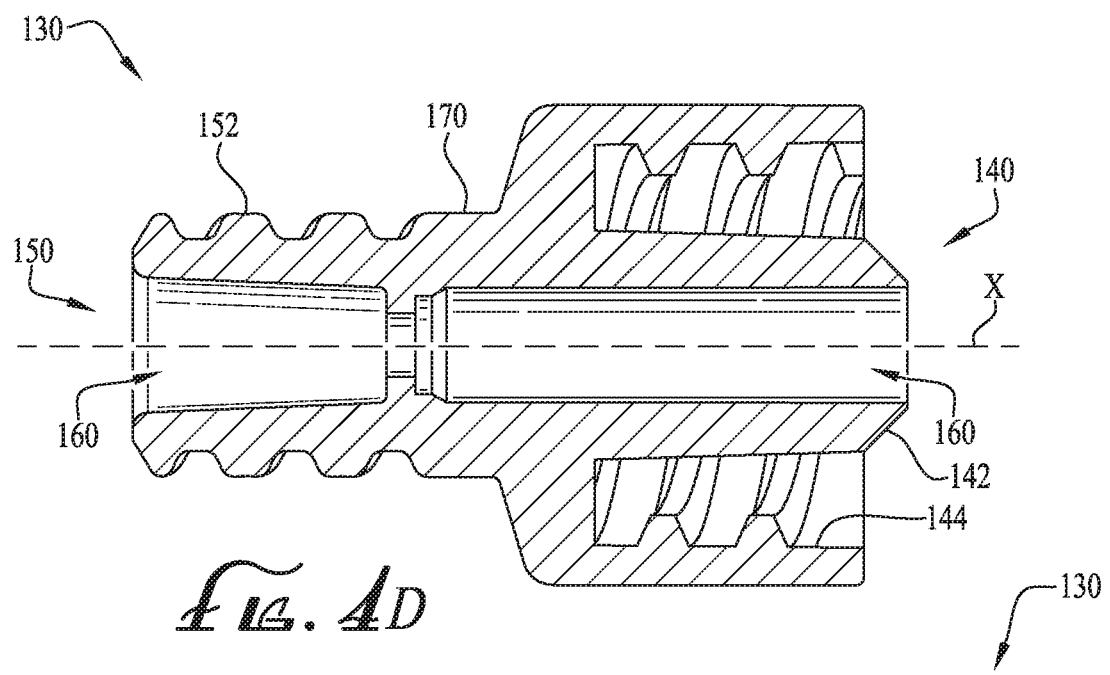
FIG. 4D
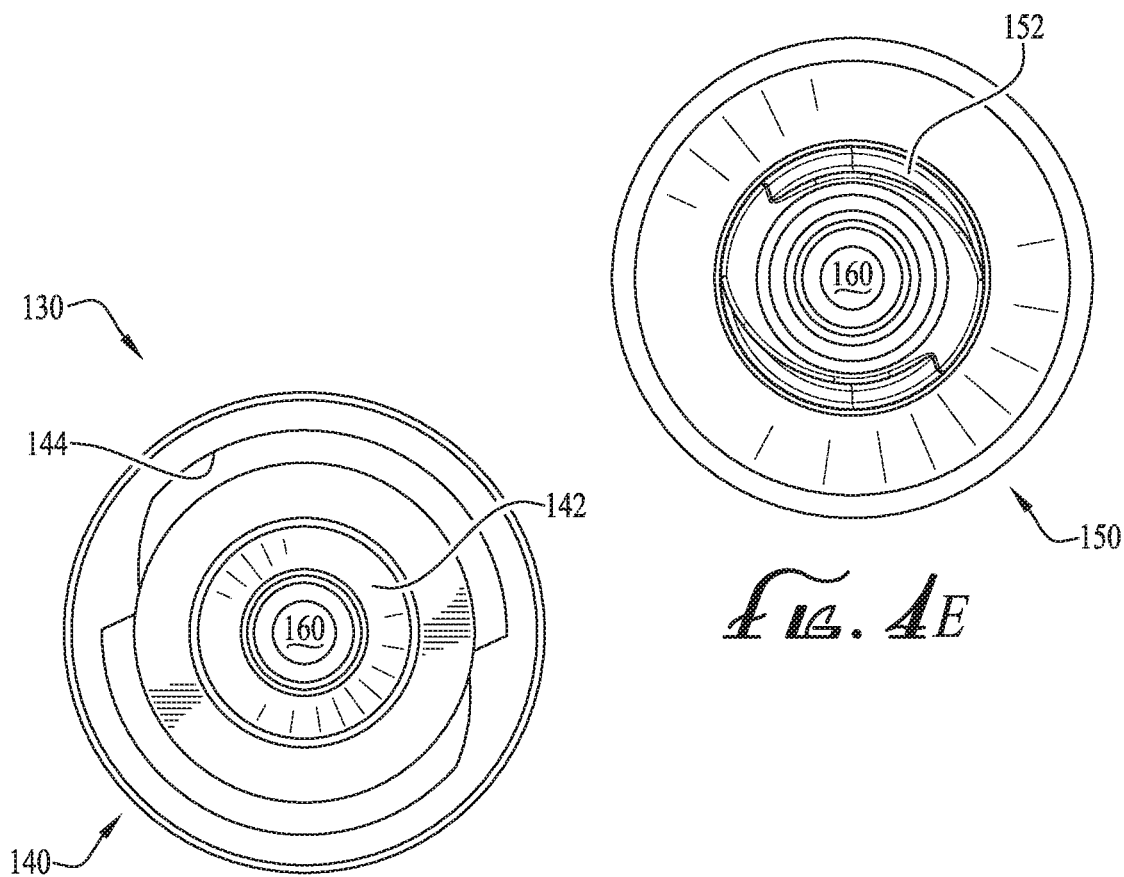
FIG. 4E
FIG. 4F

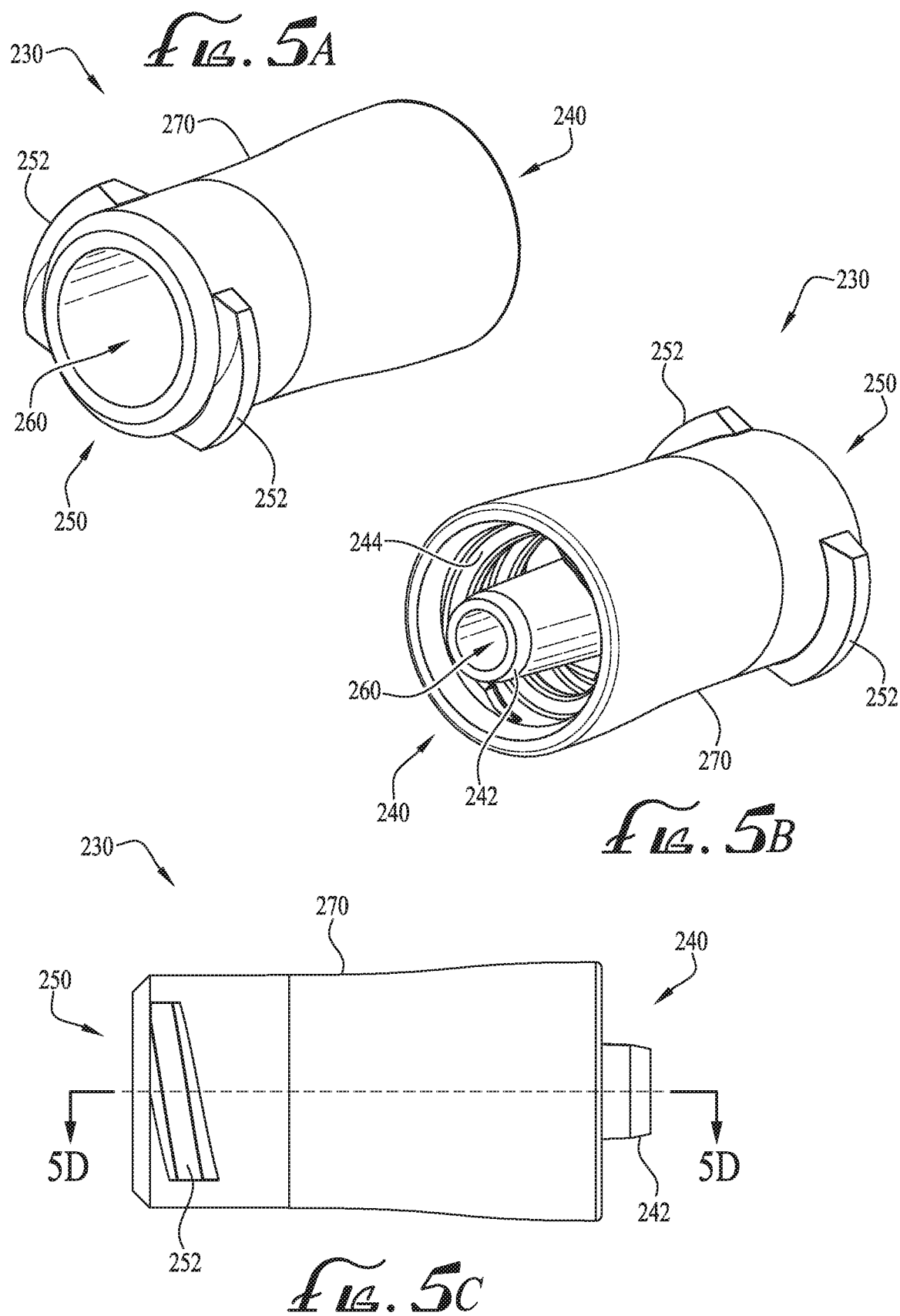

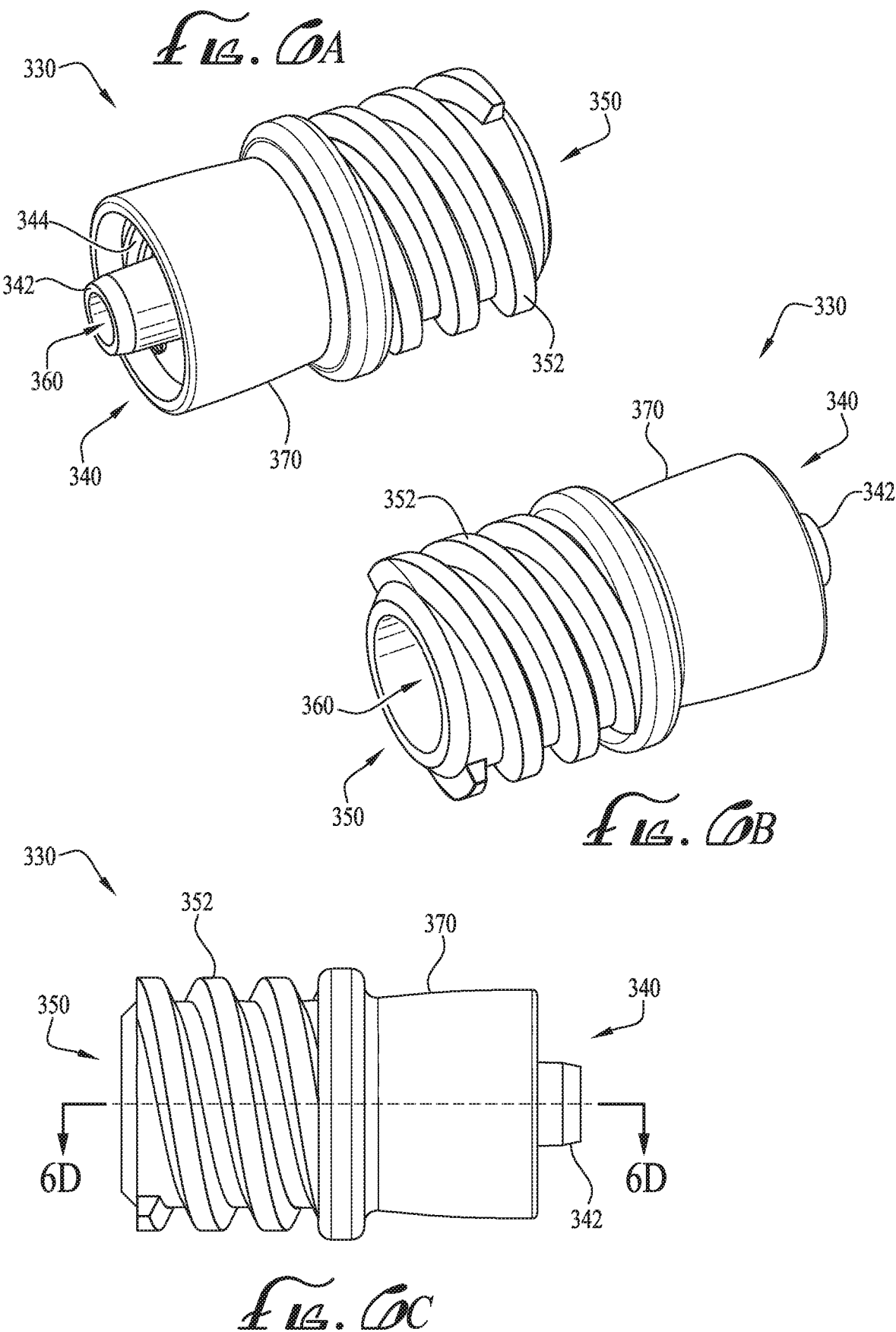

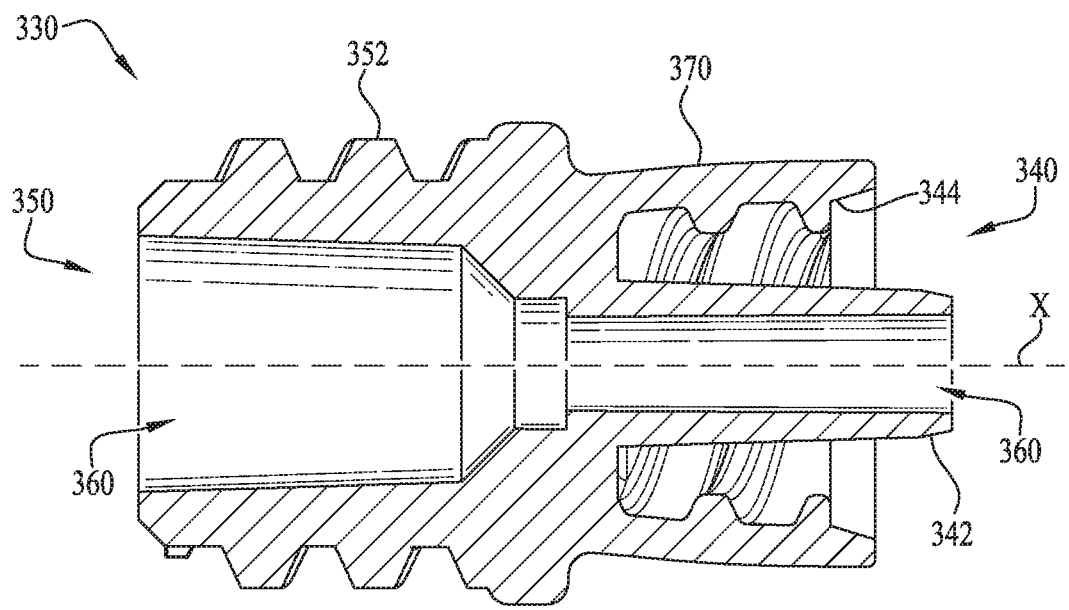
FIG. 6D
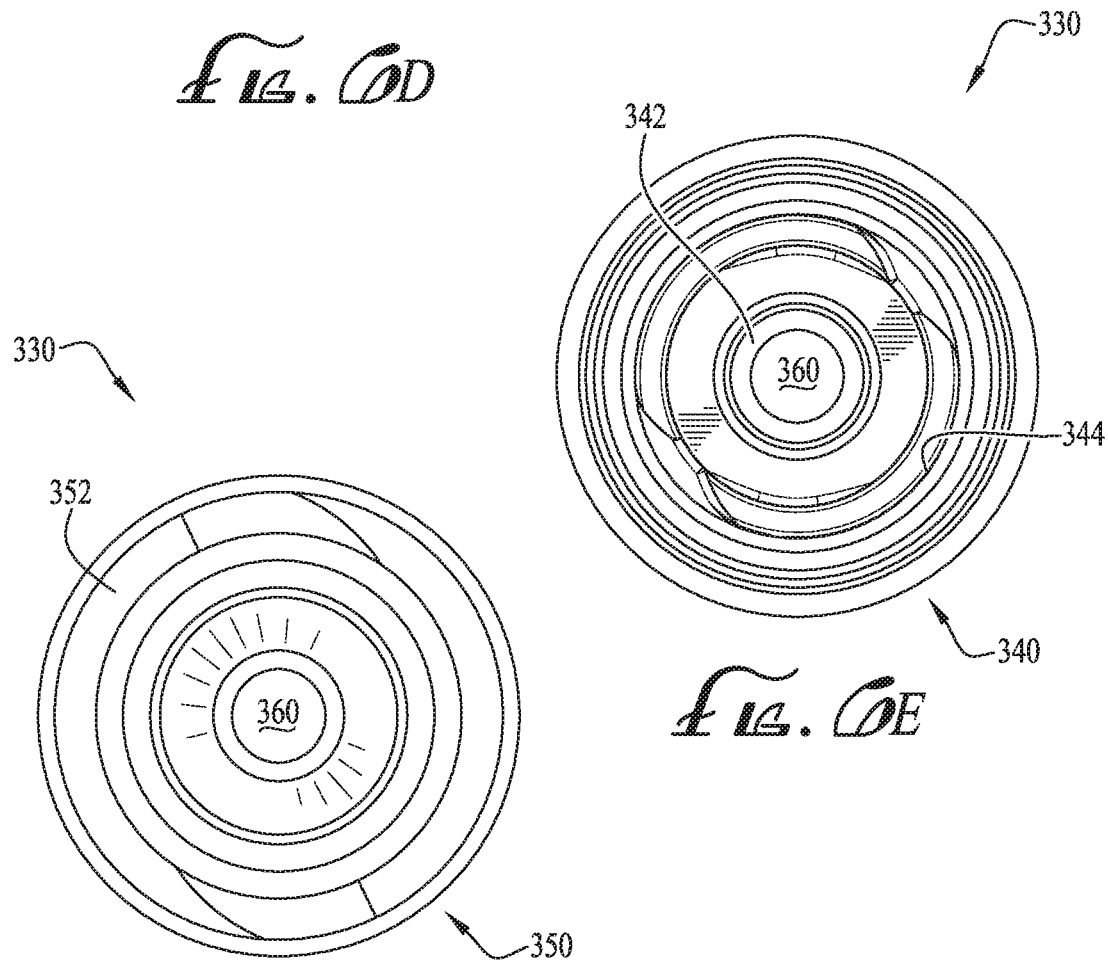
FIG. 6E
FIG. 6F

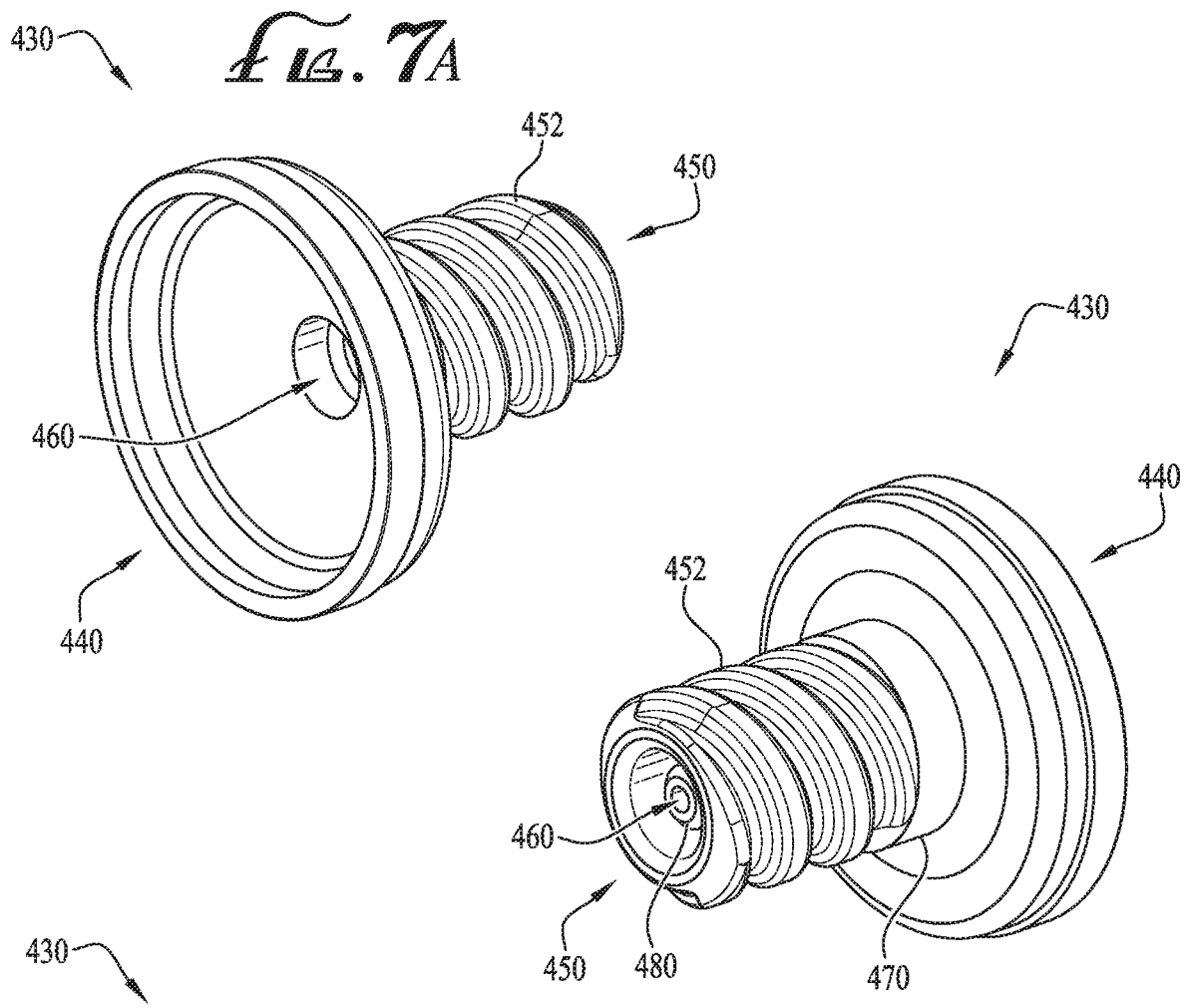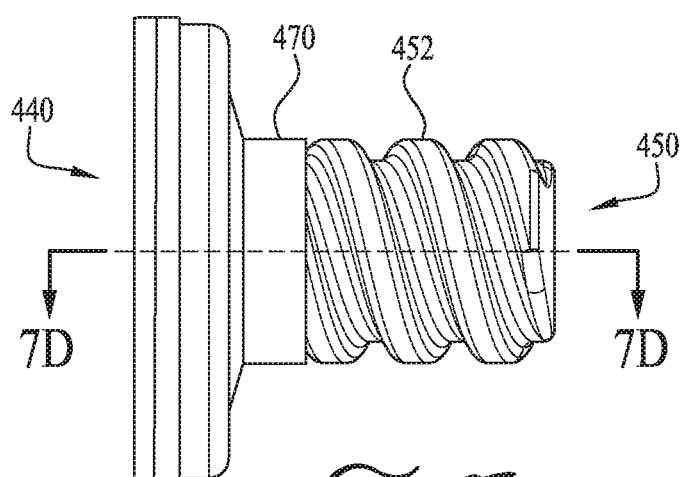

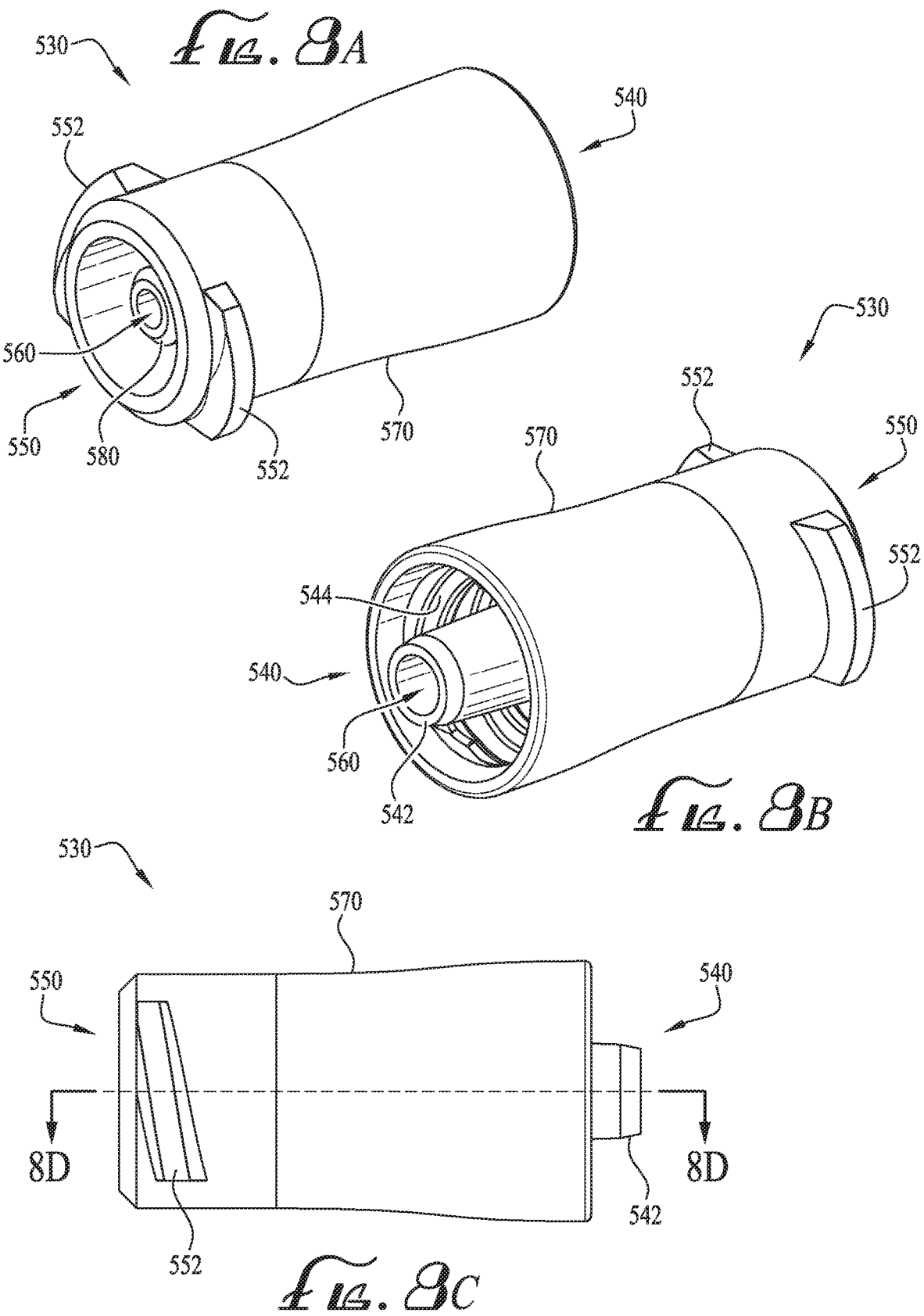

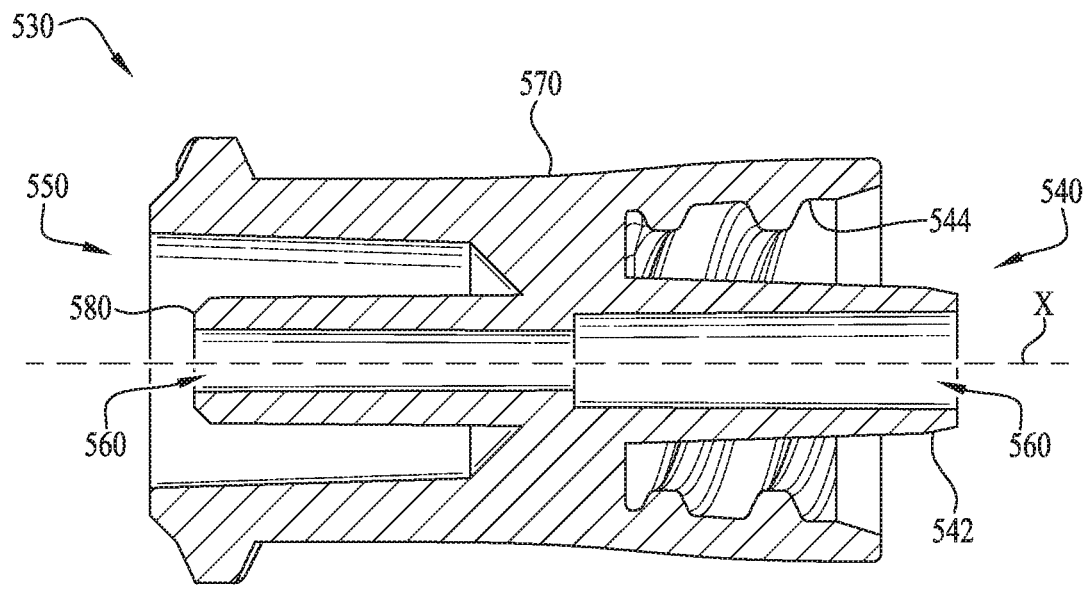
FIG. 8D
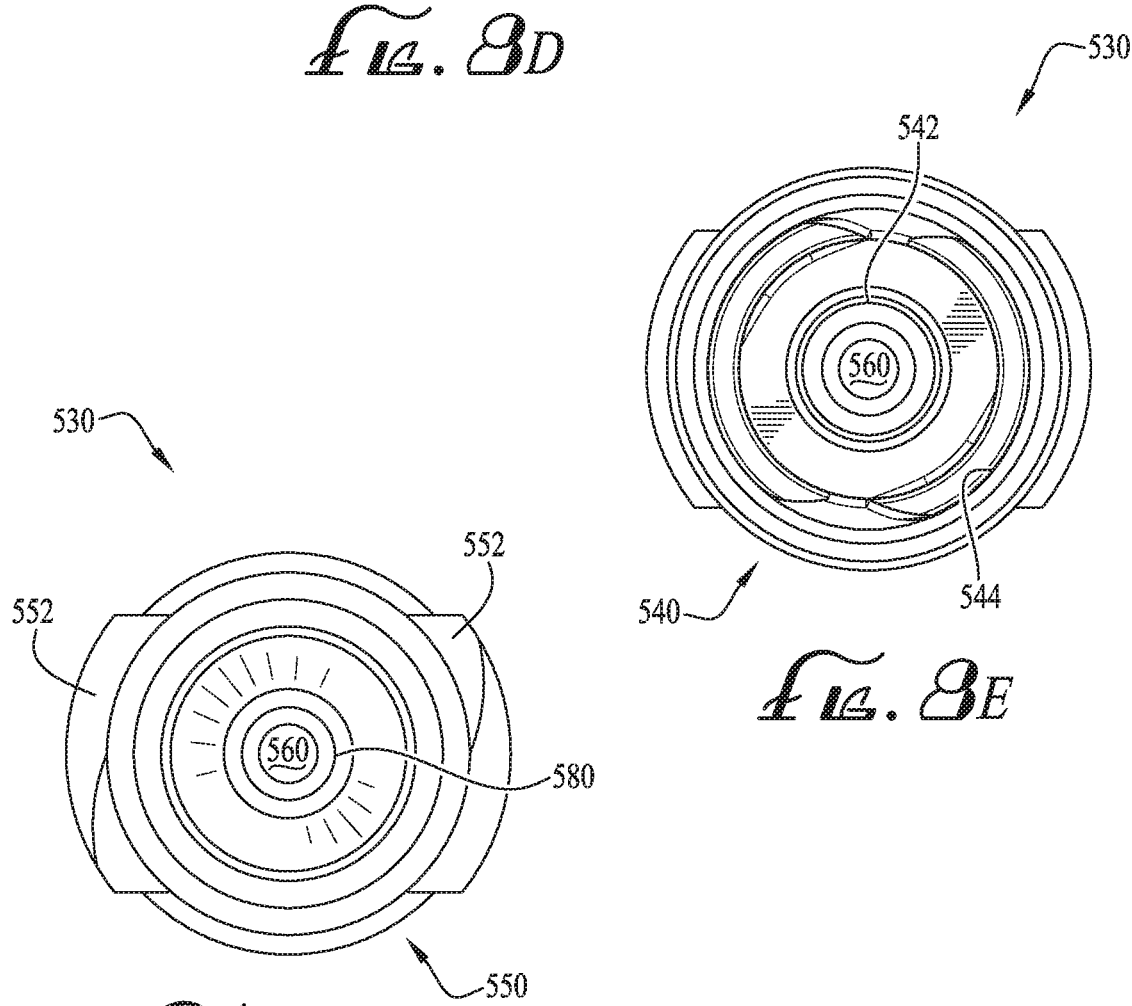
FIG. 8E
FIG. 8F

ENTERAL ADAPTOR COUPLINGS

CROSS REFERENCE TO RELATED APPLICATIONS

This application claims priority to U.S. Provisional Patent Application Ser. No. 62/192,759 filed Jul. 15, 2015, and U.S. Provisional Patent Application Ser. No. 62/207,123 filed Aug. 19, 2015, both of which are hereby incorporated herein by reference in their entireties.

TECHNICAL FIELD

The present invention relates generally to the field of enteral feeding and fluid transfer devices, and more particularly to adapter couplings for enteral nutrition or medication administration.

BACKGROUND

Healthcare patients and neonates are commonly administered fluids such as medication and nutrients by enteral fluid delivery systems. FIGS. 1 and 2 show examples of enteral feeding syringes and threaded enteral feeding couplings according to previously known forms.

Efforts are underway to develop new and improved standards for enteral delivery, such as the ISO 80369-3 standards for tubing connections (commonly known as ENFit®). These standards provide for new connector formats for enteral feeding devices that prevent misconnection to non-enteral connectors such as standard Luer connectors.

SUMMARY

The present invention is related to couplings for enteral fluid delivery systems. In example forms, the couplings allow connection between previously known non-ENFit connector formats and ISO 80369-3 compliant and compatible connectors and equipment.

In one aspect, the present invention relates to an enteral adapter coupling including a first end substantially corresponding to an ISO 80369-3 compliant coupling format, a second end substantially conforming to a threaded enteral feeding coupling format, and an internal lumen extending through the coupling allowing fluid communication between the first end and the second end.

In example embodiments, the first end includes a male ISO 80369-3 compliant tip having a tapered lead-in portion, surrounded by a coaxial connection collar having an internally threaded annular surface, and the second end includes a threaded surface defining a thread pitch of between about 2 mm to about 3 mm. In one example form, the thread pitch is about 2.450 mm. In example embodiments, the second end comprises a threaded tip geometry having an outer tip diameter of between about 5 mm to about 8 mm. In one example form, the outer tip diameter is about 6.675 mm.

In other example forms, the first end includes a female ISO 80369-3 compliant tip having at least a pair of helically inclined ribs extending radially from the external face of the tip. In example forms, the second end includes a male tip having a tapered lead-in portion, and being surrounded by a coaxial connection collar having an internally threaded annular surface having a coupling format that mates with and connects to the external threads of the enteral feeding coupling format.

In some example forms, the first and second ends are configured for coupling two syringes together to facilitate the transfer of fluids therebetween, wherein one of the syringes includes a female ISO 80369-3 compliant tip for engagement with the first end of the coupling and wherein the other one of the two syringes includes a cylindrical connection tip substantially conforming to the non-ENFit threaded enteral feeding coupling format for engagement with the second end of the coupling.

In another aspect, the present invention relates to a threaded enteral feeding coupling including a first end, a second end, a lumen extension tip, and a lumen. The first end is formed at the end of a syringe or removably coupled thereto. The second end includes a cylindrical connection tip, and the lumen extension tip projects axially from within the cylindrical connection tip. A lumen extends through the coupling from the first end to the second end. In example embodiments, the cylindrical connection tip includes external threads positioned along a helical path around at least a portion thereof. In one example form, the lumen extension tip is configured for fitting within an internal lumen of a male tip having a tapered lead-in portion, and being surrounded by a coaxial connection collar having an internally threaded annular surface comprising a coupling format that mates with and connects to the external threads of the cylindrical connection tip In yet another aspect, the present invention relates to a method of coupling enteral connectors of different coupling formats together. The method includes providing a coupler comprising a first end and a second end, the first end substantially corresponding to an ISO 80369-3 compliant coupling format and the second end substantially conforming to a non-ENFit threaded enteral feeding coupling format, and an internal lumen extending through the coupling allowing fluid communication between the first end and the second end; providing a first connector substantially corresponding to an ISO 80369-3 compliant coupling; providing a second connector substantially conforming to a threaded enteral feeding coupling format; coupling the first connector to the first end of the coupling; and coupling the second connector to the second end of the coupling.

These and other aspects, features and advantages of example embodiments of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of embodiments of the invention, and are not restrictive of the invention, as claimed.

BRIEF DESCRIPTION OF THE DRAWINGS

FIG. 1 shows various forms of enteral feeding syringes with threaded couplings according to previously known forms.

FIG. 2 is a cross-sectional view of one of the threaded couplings of the enteral feeding syringes of FIG. 1 taken along line 2-2.

FIG. 2A is a detailed view of a portion of the thread of the threaded coupling of FIG. 2.

FIG. 4A shows a first perspective view of an enteral adapter coupling according to another example embodiment of the present invention.

FIG. 4B shows a second perspective view of the enteral adapter coupling of FIG. 4A.

FIG. 4C shows a side view of the enteral adaptor coupling of FIG. 4A.

FIG. 4D shows a cross-sectional view of the enteral adaptor coupling of FIG. 4C taken along line 4D-4D.

FIG. 4E shows a second end view of the coupling of FIG. 4A.

FIG. 4F shows a first end view of the coupling of FIG. 4A.

FIG. 5A shows a first perspective view of an enteral adapter coupling according to another example embodiment of the present invention.

FIG. 5B shows a second perspective view of the enteral adapter coupling of FIG. 5A.

FIG. 5C shows a side view of the enteral adaptor coupling of FIG. 5A.

FIG. 6A shows a first perspective view of an enteral adapter coupling according to another example embodiment of the present invention.

FIG. 6B shows a second perspective view of the enteral adapter coupling of FIG. 6A.

FIG. 6C shows a side view of the enteral adaptor coupling of FIG. 6A.

FIG. 6D shows a cross-sectional view of the enteral adaptor coupling of FIG. 6C taken along line 6D-6D.

FIG. 6E shows a first end view of the coupling of FIG. 6A.

FIG. 6F shows a second end view of the coupling of FIG. 6A.

FIG. 7A shows a first perspective view of an enteral syringe tip according to another example embodiment of the present invention.

FIG. 7B shows a second perspective view of the enteral syringe tip of FIG. 7A.

FIG. 7C shows a side view of the enteral syringe tip of FIG. 7A.

FIG. 8A shows a first perspective view of an enteral adapter coupling according to another example embodiment of the present invention.

FIG. 8B shows a second perspective view of the enteral adapter coupling of FIG. 8A.

FIG. 8C shows a side view of the enteral adaptor coupling of FIG. 8A.

FIG. 8D shows a cross-sectional view of the enteral adaptor coupling of FIG. 8C taken along line 8D-8D.

FIG. 8E shows a first end view of the coupling of FIG. 8A.

FIG. 8F shows a second end view of the coupling of FIG. 8A.

DETAILED DESCRIPTION OF EXAMPLE EMBODIMENTS

Figure 3A:
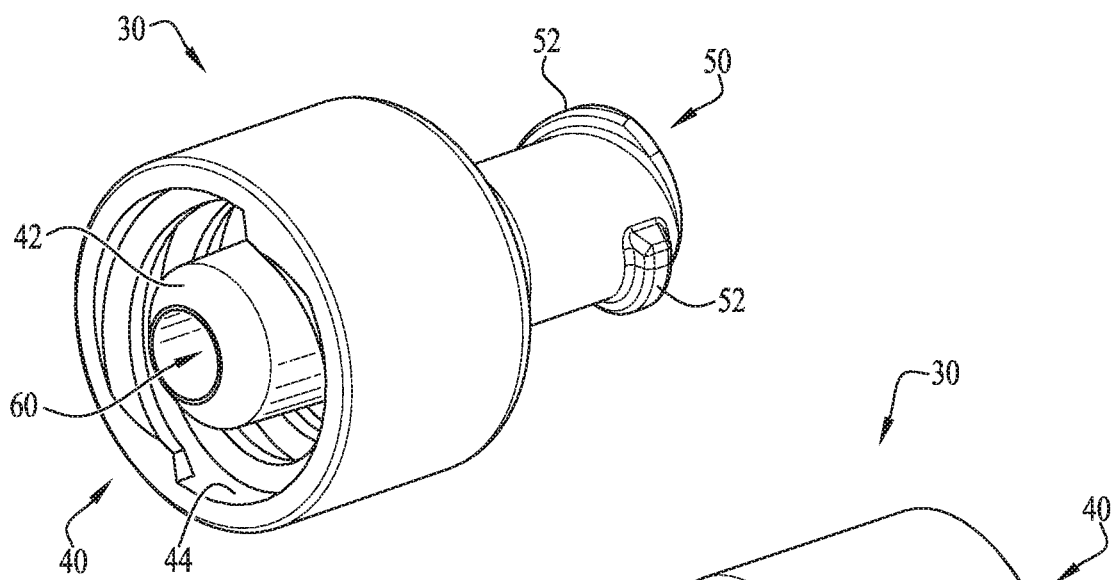
FIG. 3A shows a first perspective view of an enteral adapter coupling according to an example embodiment of the present invention.
Figure 3B:
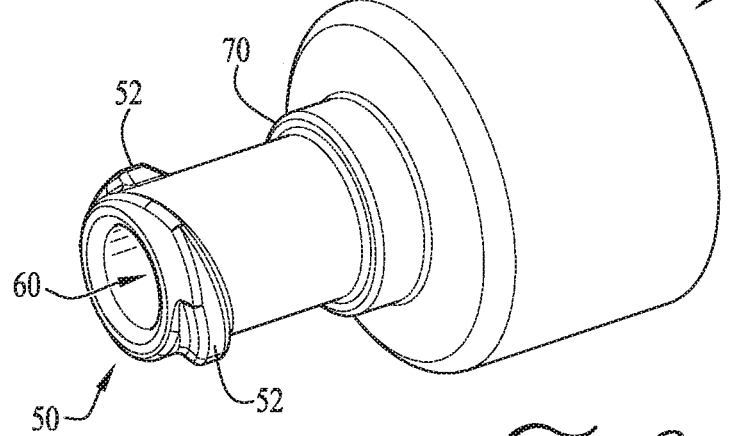
FIG. 3B shows a second perspective view of the enteral adaptor coupling of FIG. 3A.
Figure 3C:
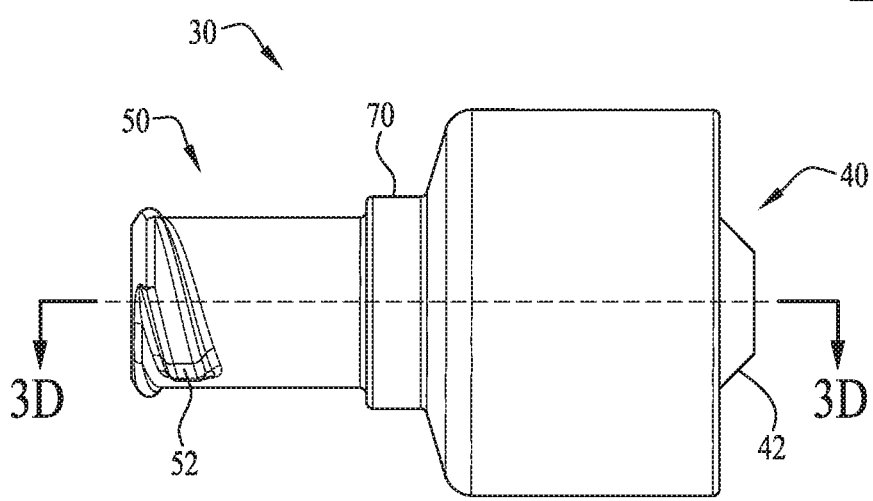
FIG. 3C shows a side view of the enteral adaptor coupling of FIG. 3A.

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIG. 1 shows a number of different size formats of enteral feeding syringes S with non-ENFit threaded coupling tips TT according to previously known forms. FIGS. 2-2A show further details of the threaded enteral feeding coupling tip TT format according to previously known forms. In example forms, the threaded tip coupling TT comprises external threads T positioned along a helical path around at least a portion of the cylindrical male tip of the syringe. In alternate forms, the threaded tip coupling comprises one or more external lugs or ribs, forming a partially threaded surface at or adjacent the tip of a syringe. According to an example form depicted in FIG. 2, the threads comprise a thread-to-thread spacing or pitch TP of between about 2.125 mm to about 2.925 mm, more preferably about 2.450 mm, a thread height TH of about 0.644 mm, and minor and major thread lengths MITL, MATL of about 1.177 mm and about 2.025 mm respectively; and the threaded tip geometry comprises an outer tip diameter D1 of about 6.675 mm, an inner lumen diameter D2 tapering between about 2.94 mm and about 3.428 mm, an internal throat diameter D3 of about 1.591 mm, a hub-to-tip length HTL of about 9.269 mm, an overall tip length OTL of about 9.687 mm, a threaded tip length TTL of about 6.441 mm, and a tip radius TR of about 0.400 mm. In alternate embodiments, one or more of the dimensions may vary, for example, by between about ±1-35%. In some example forms, the threaded tip is integrally formed with the syringe. Alternatively, a separate threaded collar can be permanently or removably mounted onto the tip of an unthreaded syringe to form the threaded tip.

In example embodiments, the couplings as described herein can comprise ISO 80369-3 compliant and compatible couplings, for example, a male or a female coupling substantially conforming to the ISO 80369-3 standard or format. Accordingly, according to some example embodiments, at least one end of the couplings (as will be described below) can be both compliant and compatible with the ISO 80369-3 standard. In alternate embodiments, one or more ends of the couplings can be either compliant or compatible. As such, the ISO 80369-3 format portions of the couplings are adapted for enteral-only applications, and preferably are not connectable or compatible with Luer-type couplings or connectors or other non-enteral-only products.

FIGS. 3A-3F show an example form of an enteral adapter coupling 30 according to the present invention. The adapter coupling 30 generally comprises a first end 40 corresponding to an ISO 80369-3 format coupling, and a second end 50 substantially conforming to a non-ENFit threaded enteral feeding coupling format, for example as described above with reference to FIGS. 1 and 2. An internal lumen 60 extends generally axially along an axis X (see FIG. 3D) through the coupling 30, to provide fluid communication between the first end 40 and the second end 50. In the depicted embodiment, the first end 40 comprises a male ISO 80369-3 format tip 42 having a tapered lead-in portion, surrounded by a coaxial connection collar 44 having an internally threaded annular surface. In alternate embodiments, the first end may comprise a female ISO 80369-3 format tip (as will be described below), or other coupling format. The second end 50 comprises a pair of partial thread lugs or helically inclined ribs 52 extending radially from the external face of the tip, for example having a thread pitch, size and geometry corresponding to the coupling format disclosed with reference to FIG. 2 above. A central body extension portion 70 is optionally provided between the first end 40 and the second end 50, to vary the length of the coupling 30 as desired, and/or for engagement with connected tubing or other equipment.

Figure 3D:
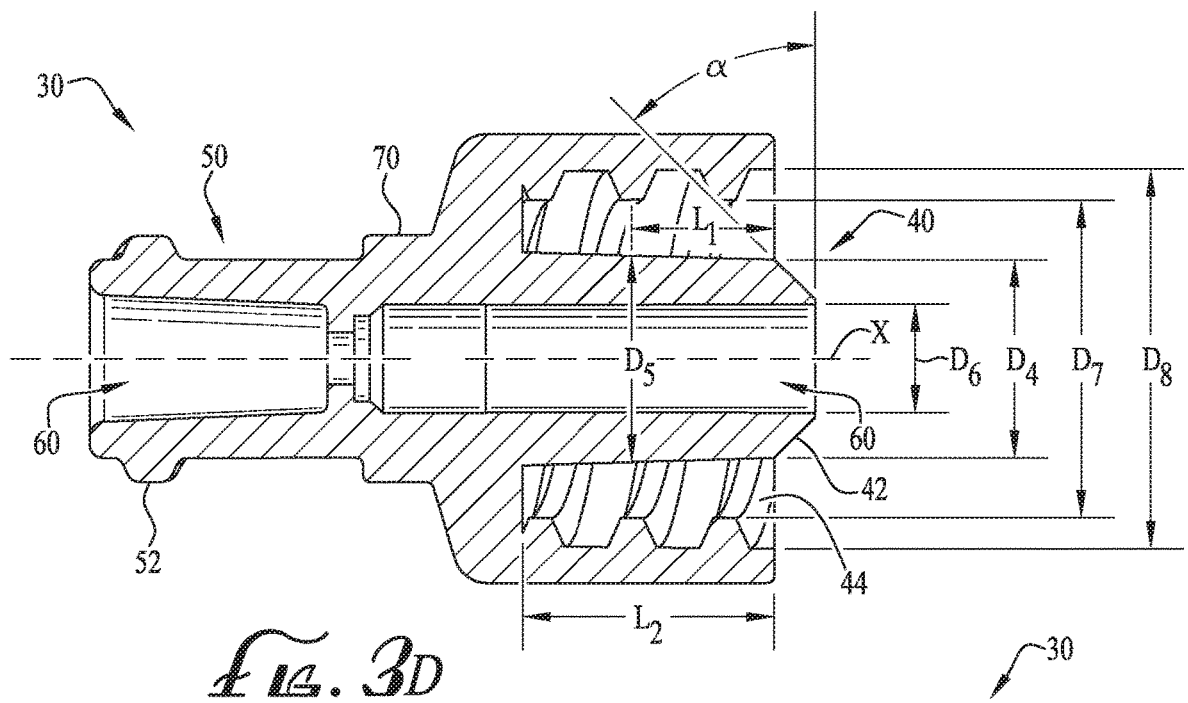
FIG. 3D shows a cross-sectional view of the enteral adaptor coupling of FIG. 3C taken along line 3D-3D.
Figure 3E:
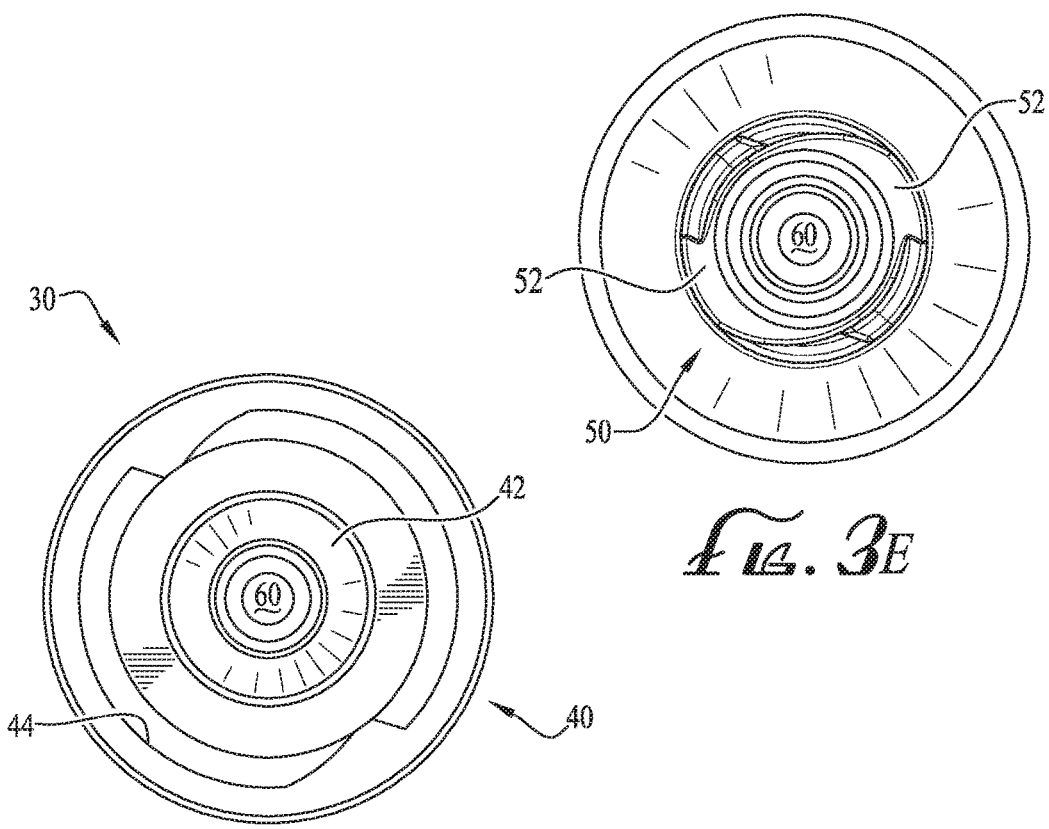
FIG. 3E shows a second end view of the coupling of FIG. 3A.
Figure 3F:
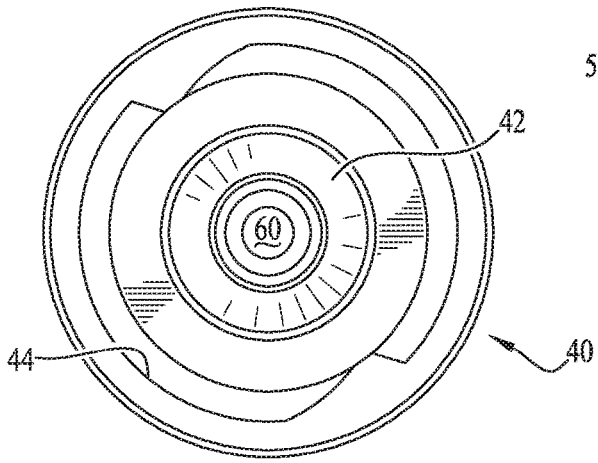
FIG. 3F shows a first end view of the coupling of FIG. 3A
Figure 5D:
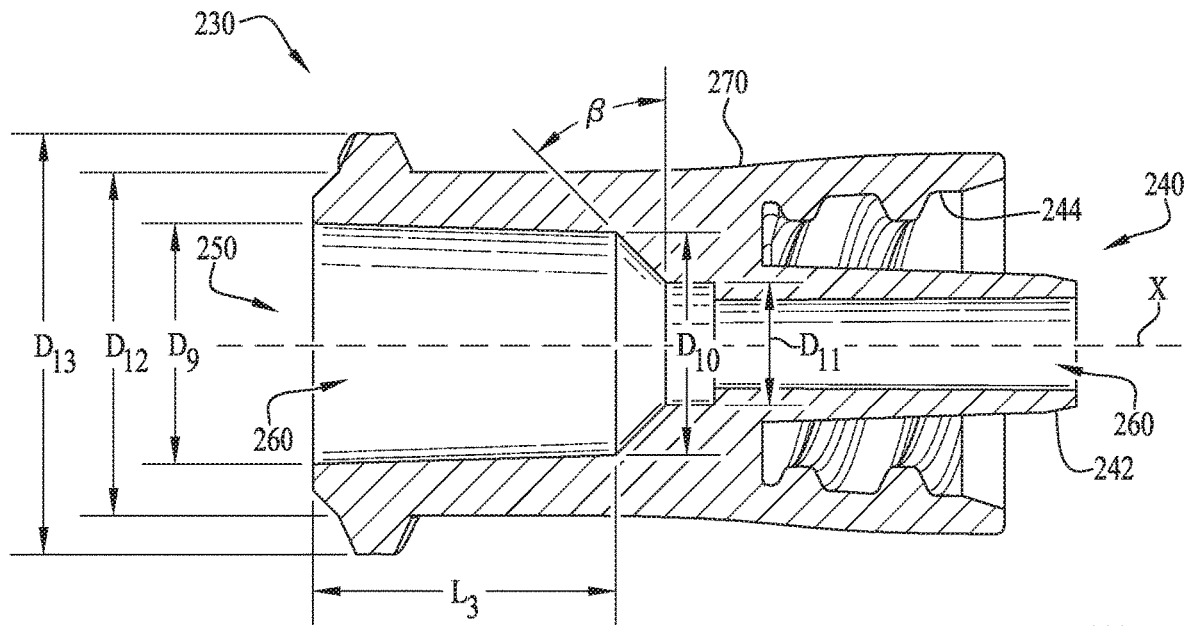
FIG. 5D shows a cross-sectional view of the enteral adaptor coupling of FIG. 5C taken along line 5D-5D.
Figure 5E:
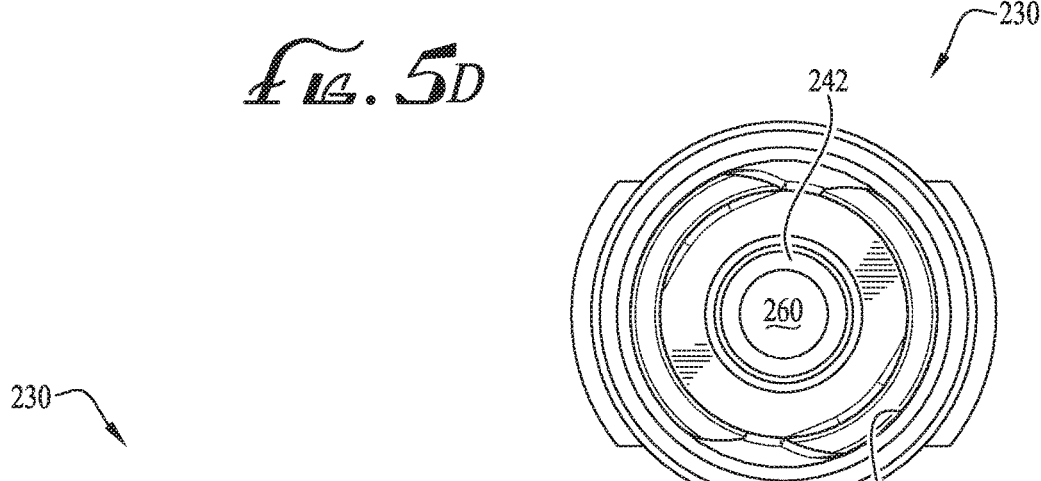
FIG. 5E shows a first end view of the coupling of FIG. 5A.
Figure 5F:
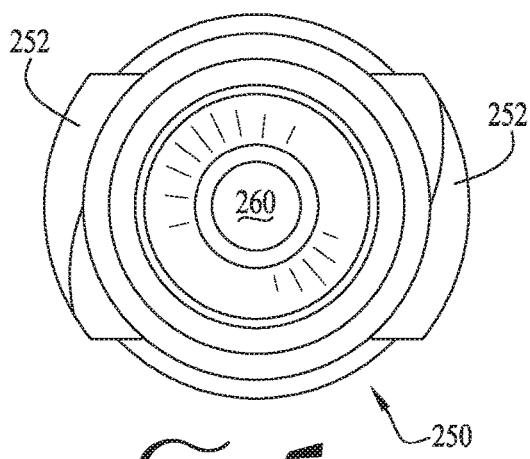
FIG. 5F shows a second end view of the coupling of FIG. 5A.
Figure 7D:
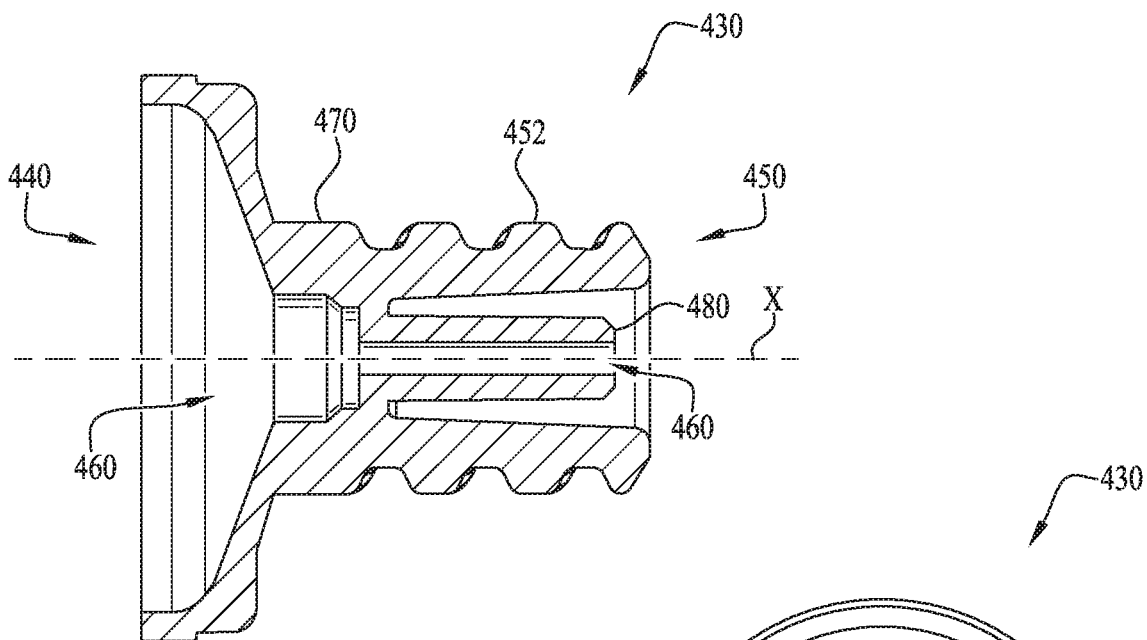
FIG. 7D shows a cross-sectional view of the enteral syringe tip of FIG. 7C taken along line 7D-7D.
Figure 7E:
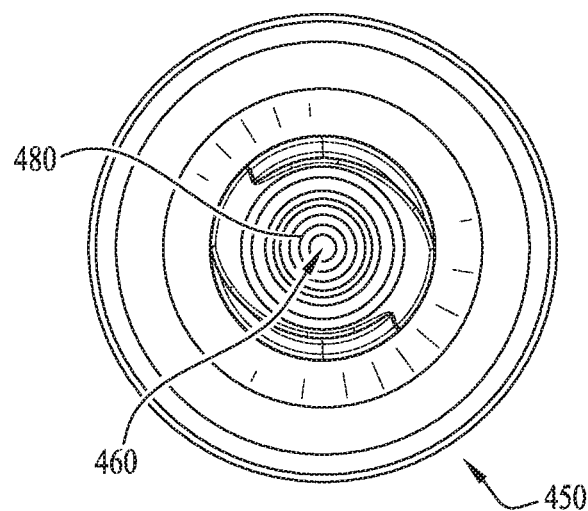
FIG. 7E shows a second end view of the coupling of FIG. 7A.
Figure 7F:
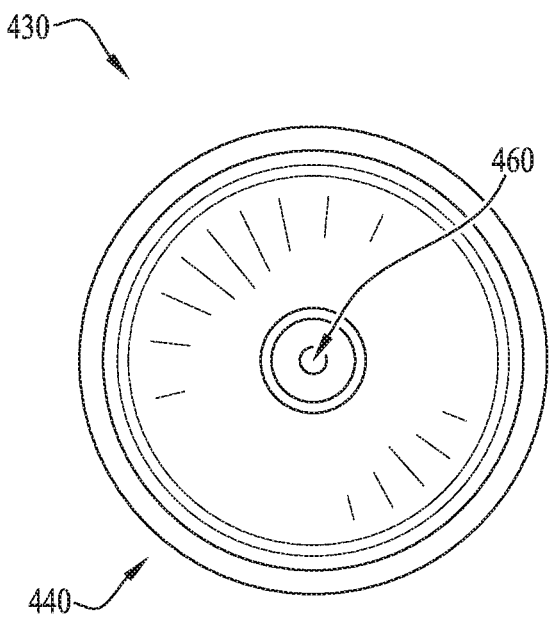
FIG. 7F shows a first end view of the coupling of FIG. 7A.

In example embodiments, the first end 40 is preferably compatible with the ISO 80369-3 standard. For example, according to example embodiments and as depicted in FIG. 3D, the first end 40 of the tip 42 comprises a first outer diameter D4 that is defined at an end of the tip 42 adjacent the beginning of the tapered or chamfered surface (defined by angle α) and a second outer diameter D5 that is defined at a length L1 from the end of the tip 42 adjacent the taper. The internal lumen of the tip 42 is defined by a diameter D6. In example embodiments, the coaxial connection collar 44 comprises a minor inside thread diameter D7 and a major inside thread diameter D8. In example forms, the length of the tip 42 from the end of the coaxial connection collar is defined by a length L2. In example embodiments, the first outer diameter D4 is about 5.41 millimeters, the second outer diameter D5 is about 5.64 millimeters, the internal lumen diameter D6 is about 2.90 millimeters, the minor inside thread diameter D7 is about 8.65 millimeters, and the major inside thread diameter D8 is about 10.23 millimeters. In some example forms, the diameter D8 is larger than 10.23 millimeters, for example, wherein the male hub H generally relies on frictional engagement with the coupling 40 (e.g., instead of the lugs 44 engaging the internally threaded annular surface of the connection collar). The length L1 is about 3.82 millimeters, the length L2 is about 6.82 millimeters or greater, and the angle α of the taper is about 45 degrees.

FIGS. 4A-4F show another example form of an enteral adapter coupling 130 according to the present invention. The adapter coupling 130 generally comprises a first end 140 corresponding to an ISO 80369-3 format coupling, and a second end 150 substantially conforming to a non-ENFit threaded enteral feeding coupling format, for example as described above with reference to FIGS. 1 and 2. An internal lumen 160 extends generally axially along an axis X (see FIG. 4D) through the coupling 130, to provide fluid communication between the first end 140 and the second end 150. In the depicted embodiment, the first end 140 comprises a male ISO 80369-3 format tip 142 having a tapered lead-in portion, surrounded by a coaxial connection collar 144 having an internally threaded annular surface. In alternate embodiments, the first end 140 may comprise a female ISO 80369-3 format tip, or other coupling format. The second end 150 comprises a helically threaded cylindrical connection tip 152, having a substantially continuous external threaded surface along at least a portion of its length, for example having a thread pitch, size and geometry corresponding to the coupling format disclosed with reference to FIG. 2 above. A central body extension portion 170 is optionally provided between the first end 140 and the second end 150, to vary the length of the coupling 130 as desired, and/or for engagement with connected tubing or other equipment.

FIGS. 5A-5F show another example form of an enteral adapter coupling 230 according to the present invention. The adapter coupling 230 generally comprises a first end 240 having an internally threaded portion comprising a coupling format that mates with and connects to the external threads of the enteral feeding coupling format, for example as described above with reference to FIGS. 1 and 2, and a second end 250 corresponds to an ISO 80369-3 format coupling. In example forms, the first end 240 comprises a male tip 242 having a tapered lead-in portion, surrounded by a coaxial connection collar 244 having an internally threaded annular surface, for example, which comprises a thread pitch, size and geometry corresponding to the coupling format disclosed with reference to FIG. 2 above.

In example forms, the male tip 242 is generally shaped and sized to become engaged within the inner lumen of the threaded tip coupling TT when the threaded tip coupling TT is mated and connected with the first end 240 of the coupling 230. The second end 250 comprises a female ISO 80369-3 format tip which comprises a pair of partial thread lugs or helically inclined ribs 252 extending radially from the external face of the tip for providing engagement with a male ISO 80369-3 format tip having a tapered lead-in portion, and surrounded by the coaxial connection collar having an internally threaded annular surface. An internal lumen 260 extends generally axially along a lengthwise axis X (see FIG. 5D) through the coupling 230, to provide fluid communication between the first end 240 and the second end 250. A central body extension portion 270 is optionally provided between the first end 240 and the second end 250, to vary the length of the coupling 230 as desired, and/or for engagement with connected tubing or other equipment.

In example embodiments, the second end 250 is compatible with the ISO 80369-3 standard, for example, to provide for coupling engagement with a male ISO 80369-3 format coupling (and the male tip 42 thereof, see FIG. 3D). The female ISO 80369-3 format tip comprises a first internal diameter D9 and a second internal diameter D10 that are spaced a length L3 between each other. An angled taper (defined by an angle β) is provided generally adjacent the second internal diameter D10, and a medial conduit provided generally near the taper defines an internal diameter D10. The lugs 252 define a minor outside thread diameter D12 and a major outside thread diameter D13. According to example embodiments, the first internal diameter D9 is about 5.69 millimeters, the second internal diameter D10 is about 5.26 millimeters, the inner diameter D11 is about 2.90 millimeters, the minor outside thread diameter D12 is about 8.10 millimeters, and the major outside thread diameter D13 is about 9.93 millimeters. The length L3 defined between the first and second internal diameters D9, D10 is about 7.14 millimeters, and the angle β of the angled taper is about 45 degrees. Optionally, according to alternate example forms, the female ISO 80369-3 format coupling of the second end 250 can be sized and shaped as desired.

FIGS. 6A-6F show another example form of an enteral adapter coupling 330 according to the present invention. The adapter coupling 330 generally comprises a first end 340 having an internally threaded portion comprising a coupling format that mates with and connects to the external threads of a non-ENFit enteral feeding coupling format, for example as described above with reference to FIGS. 1 and 2, and a second end 350 corresponding to an ISO 80369-3 format coupling. In example forms, the first end 340 comprises a male tip 342 having a tapered lead-in portion, surrounded by a coaxial connection collar 344 having an internally threaded annular surface, for example, which comprises a thread pitch, size and geometry corresponding to the coupling format disclosed with reference to FIG. 2 above. The second end 350 comprises a female ISO 80369-3 format tip comprising threads or helically inclined ribs or ridges 352 extending radially from the external face of the tip for providing engagement with the internally threaded annular surface of the male ISO 80369-3 format tip. An internal lumen 360 extends generally axially along a lengthwise axis X (see FIG. 6D) through the coupling 330, to provide fluid communication between the first end 340 and the second end 350. A central body extension portion 370 is optionally provided between the first end 340 and the second end 350, to vary the length of the coupling 330 as desired, and/or for engagement with connected tubing or other equipment.

In an example method of use, a coupling according to the present invention may be attached to an ISO 80369-3 format syringe or other enteral device by attachment of the first end of the coupling to an ISO 80369-3 format coupling of the syringe or other enteral device, for example a female ISO 80369-3 format coupling. And the second end of the coupling may be attached to a feeding tube or other enteral device having a non-ENFit threaded coupling format, for example as disclosed above with reference to FIGS. 1 and 2. Alternatively, the coupling may be used to couple an enteral syringe having a threaded tip according to a previously known threaded connection format to an ISO 80369-3 format feeding tube, connectors or other enteral equipment. Nutritional fluids, medication or other enteral fluids may then be administered from the syringe, through the coupling, to the feeding tube, and to a neonate or other human or animal patient. In this manner, the coupling of the present invention adapts previously known non-ENFit enteral equipment for use in connection with newly developed ISO 80369-3 format enteral equipment.

FIGS. 7A-7F shows a threaded enteral feeding coupling 430 according to another example embodiment of the present invention. As depicted, the coupling 430 is generally similar to the coupling as depicted in FIG. 2. In example forms, the coupling 430 generally comprises a first end 440 and a second end 450. In some example forms, the first end 440 is integrally formed with the syringe. Alternatively, the first end 440 can be permanently or removably mounted onto the tip of an unthreaded syringe to form a threaded tip. The second end 450 substantially conforms to a threaded enteral feeding coupling format, for example as described above with reference to FIGS. 1 and 2. In example forms, the second end 450 comprises a helically threaded cylindrical connection tip 452, having a substantially continuous external threaded surface along at least a portion of its length, for example having a thread pitch, size and geometry corresponding to the coupling format disclosed with reference to FIG. 2 above. A central body extension portion 470 is optionally provided between the first end 440 and the second end 450, with a length selected to increase the length of the coupling 430 as desired, and/or with a length and an outer surface for engagement (e.g., friction fit) with connected tubing or other equipment.

An internal lumen 460 extends generally axially along a lengthwise axis X (see FIG. 7D) through the coupling 430, to provide fluid communication between the first end 440 and the second end 450. In example forms, a lumen extension tip 480 (generally having a tapered lead-in portion) projects axially from within the cylindrical connection tip 452 in a direction generally opposite the first end 440. Preferably, the lumen extension tip 480 is adapted and configured for being received within a tip (e.g., the internal lumen) of a male coupling (as will be described below), for example, such that dosing inconsistencies and anomalies in accuracy during fluid delivery are reduced, minimized or substantially eliminated. In example forms, the length of the lumen extension tip 480 is at least partially less than the length of the cylindrical connection tip 452, for example, such that the lumen extension tip 480 is optionally recessed inwardly, and positioned generally coaxially and concentrically within the cylindrical connection tip 452. U.S. Provisional Patent Application Ser. No. 62/350,934 is incorporated herein by reference and discloses lumen extension tips for reducing, minimizing, or substantially eliminating dosing inconsistencies and anomalies in accuracy during fluid delivery.

In example embodiments, the length of the lumen extension tip 480 is generally less than the length of the tip of the second end 450 such that the lumen extension tip 480 is generally recessed within the tip of the second end 450, or for example, the end of the lumen extension tip 480 generally remains at a position below the outer edge or conical rim of the second end 450. In some example embodiments, the size, shape, position, etc. of the lumen extension tip 480 is generally configured for seating within the internal lumen of the male tip of a coupling, for example, within the internal lumen 260 of the male tip 242 of the first end 240 of the coupling 230 of FIG. 5D (e.g., generally having an internally threaded portion comprising a coupling format that mates with and connects to the external threads of the enteral feeding coupling format, for example as described above with reference to FIGS. 1 and 2). Optionally, the lumen extension tip 480 can be sized and shaped as desired.

FIGS. 8A-8F show another example form of an enteral adapter coupling 530 according to the present invention. The adapter coupling 530 generally comprises a first end 540 having an internally threaded portion 544 comprising a coupling format that mates with and connects to the external threads of the enteral feeding coupling format, for example as described above with reference to FIGS. 1 and 2 (see also FIGS. 7A-E), and a second end 550 corresponding to an ISO 80369-3 format coupling. An internal lumen 560 extends generally axially along an axis X (see FIG. 8D) through the coupling 530, to provide fluid communication between the first end 540 and the second end 550.

In the depicted embodiment, the first end 540 comprises a male tip 542 having a tapered lead-in portion, surrounded by a coaxial connection collar 544 having an internally threaded annular surface. In example forms, the male tip 542 is generally sized, shaped and adapted for receiving the lumen extension tip 480 of the coupling 430 (as described above), for example, whereby the lumen extension tip 480 is generally fitted within the lumen 560 of the male tip 542 when the cylindrical connection tip 452 is removably coupled to the threaded annular surface of the coaxial connection collar 544.

The second end 550 comprises a pair of partial thread lugs or helically inclined ribs 552 extending radially from the external face of the tip, for example having a thread pitch, size and geometry substantially conforming to the ISO 80369-3 standards for tubing connections. A central body extension portion 570 is optionally provided between the first end 540 and the second end 550, to vary the length of the coupling 530 as desired, and/or for engagement with connected tubing or other equipment. In preferred example forms, the second end 550 comprises an axial lumen extension tip 580 having a tapered lead-in portion, which is provided for interengagement with a male coupling hub of an ISO 80369-3 format male coupling. In example forms, the lumen extension tip 580 projects axially from within the female ISO 80369-3 format tip in a direction generally opposite the first end 540, and defines the internal lumen 560 extending therethrough. U.S. Provisional Patent Application Ser. No. 62/350,934 is incorporated herein by reference and discloses lumen extension tips for reducing, minimizing, or substantially eliminating dosing inconsistencies and anomalies in accuracy during fluid delivery. As similarly described above, the length of the lumen extension tip 580 is generally less than the extension of the tip of the second end 550 such that the lumen extension tip 580 is generally recessed within the tip of the second end 550, or for example, the end of the lumen extension tip 580 generally remains at a position below the outer edge or conical rim of the second end. In some example embodiments, the size, shape, position, etc. of the lumen extension tip 580 is generally configured for seating within the internal lumen of an ISO 80369-3 format coupling (e.g., see internal lumen 60 of the male ISO 80369-3 format tip 42 in FIG. 3A and internal lumen 160 of the male ISO 80369-3 format tip 142 of FIG. 4A).

Thus, according to example forms of the present invention, the lumen extension tips 480, 580 are optionally provided to reduce the volume that is defined within the couplings 430, 530 such that dosing inconsistencies and anomalies in accuracy during fluid delivery are reduced, minimized or substantially eliminated. Optionally, lumen extension tips may be provided with any one or more of the other couplings as described above.

According to other example forms, the couplings as described above can be modified to provide for a dual-action installation and removal mechanism, for example, wherein the engagement or attachment provided between at least one of the ends of the coupling and a compatible connector can either be rotationally connected as described above, or can be configured such that a direct, push or snap-on engagement (e.g., generally axial movement therebetween) connects one of the ends and a compatible connector together. According to one example embodiment, the coaxial connection collar is modified to comprise a radial array of two or more split retainer tab members or clips, which are generally at least partially flexible and resilient for outwardly flexing during engagement with the outer threads of the coupling of FIGS. 1 and 2. U.S. patent application Ser. Nos. 15/078,674, 15/185,583, and 14/844,922, U.S. Design patent application Ser. Nos. 29/521,665 and 29/533,173 are incorporated herein by reference and disclose various clipped, snap-on and dual-action attachment and removal mechanisms. Optionally, one or more of the ends of the couplings can be provided with tabs or clips for providing permanent engagement between the coupling and the compatible connector, for example, when it is intended to prevent removal of the coupling with the compatible connector after use.

According to another example embodiment of the present invention, the coupling can be configured for coupling syringes of different coupling formats (e.g., for coupling a syringe comprising an ISO 80369-3 format coupling format with a syringe comprising a threaded coupling tip TT of FIGS. 1-2). For example, according to one example form, the first end of the coupling comprises an internally threaded portion comprising a coupling format that mates with and connects to the external threads of the enteral feeding coupling format, for example as described above with reference to FIGS. 1 and 2 (see first end 240 of coupling 230). And, the second end of the coupling comprises a male ISO 80369-3 format tip having a tapered lead-in portion, surrounded by a coaxial connection collar having an internally threaded annular surface that mates and connects with a female ISO 80369-3 format tip. Thus, the coupling can be configured for facilitating the transfer of fluids between syringes of different coupling formats, for example, between an ISO 80369-3 format coupling and a threaded coupling tip TT.

In another example embodiment, the present invention relates to a method of coupling enteral connectors of different coupling formats together, for example, for coupling a connector having an ISO 80369-3 format coupling format with a connector having a threaded enteral feeding coupling format as described above with reference to FIGS. 1 and 2. In example forms, the method includes providing a coupler comprising a first end and a second end, the first end substantially corresponding to an ISO 80369-3 format coupling format and the second end substantially conforming to a threaded enteral feeding coupling format, and an internal lumen extending through the coupling allowing fluid communication between the first end and the second end; providing a first connector substantially corresponding to an ISO 80369-3 format coupling; providing a second connector substantially conforming to a threaded enteral feeding coupling format; coupling the first connector to the first end of the coupling; and coupling the second connector to the second end of the coupling.

While the invention has been described with reference to example embodiments, it will be understood by those skilled in the art that a variety of modifications, additions and deletions are within the scope of the invention, as defined by the following claims.

What is claimed is:

1. An enteral adaptor coupling comprising:
   a first end, a second end, and an internal lumen extending between the first end and the second end allowing fluid communication between the first end and the second end, the first end comprising a threaded portion formed thereon and the second end comprising a threaded portion formed thereon, the first end substantially corresponding to an ISO 80369-3 compliant coupling format, and the second end substantially conforming to a threaded enteral feeding coupling format,
   wherein the internal lumen extends along a longitudinal axis, further wherein the internal lumen comprises a first lumen section at the first end having a constant internal diameter, a second lumen section at the second end having a tapered internal diameter, and a third lumen section disposed between the first lumen section and the second lumen section along the longitudinal axis and having a constant internal diameter, wherein the constant internal diameter of the third lumen section is not equal to internal diameter of the first lumen section or any internal diameter of the tapered second lumen section.

2. The enteral adaptor coupling of claim 1, wherein the first end comprises a male ISO 80369-3 compliant tip having a tapered lead-in portion, surrounded by a coaxial connection collar having an internally threaded annular surface.

3. The enteral adaptor coupling of claim 1, further comprising a body extension portion provided between the first end and the second end.

4. The enteral adaptor coupling of claim 1, wherein the thread pitch of the threaded portion of the second end is between about 2 mm to about 3 mm.

5. The enteral adaptor coupling of claim 1, wherein the threaded portion of the second end is defined on an exterior portion thereof.

6. The enteral adaptor coupling of claim 5, wherein the outer tip diameter is about 6.675 mm.

7. The enteral adaptor coupling of claim 1, wherein the second end comprises a tip geometry having a tip length of between 8 mm to 11 mm.

8. The enteral adaptor of claim 7, wherein the tip length is about 9.687 mm.

9. The enteral adaptor coupling of claim 1, wherein the first end comprises a female ISO 80369-3 compliant tip having at least a pair of helically inclined ribs extending radially from the external face of the tip.

10. The enteral adaptor coupling of claim 9, wherein the second end comprises a male tip having a tapered lead-in portion, and being surrounded by a coaxial connection collar having an internally threaded annular surface comprising a thread pitch of between about 2 mm to about 3 mm.

11. The enteral adaptor coupling of claim 9, further comprising a lumen extension tip projecting axially from within the female ISO 80369-3 compliant tip in a direction generally opposite the second end, and defining the internal lumen extending therethrough.

12. The enteral adaptor coupling of claim 2, wherein the second end comprises a male tip having a tapered lead-in portion, and being surrounded by a coaxial connection collar having an internally threaded annular surface comprising a thread pitch of between about 2 mm to about 3 mm.

13. The enteral adaptor coupling of claim 12, wherein the first and second ends are configured for coupling two syringes together to facilitate the transfer of fluids therebetween, wherein one of the syringes comprises a female ISO 80369-3 compliant tip for engagement with the first end of the coupling and wherein the other one of the two syringes comprises a cylindrical connection tip substantially conforming to the threaded enteral feeding coupling format for engagement with the second end of the coupling.

14. A threaded enteral feeding coupling comprising:
a first end formed at the end of a syringe or removably coupled thereto, the first end comprising an ISO 80369-3 compliant coupling format;
a second end comprising a non-ISO 80369-3 compatible cylindrical connection tip; and
a lumen extending through the coupling from the first end to the second end,
wherein the internal lumen extends along a longitudinal axis, further wherein the internal lumen comprises a first lumen section at the first end having a constant internal diameter, a second lumen section at the second end having a tapered internal diameter, and a third lumen section disposed between the first lumen section and the second lumen section along the longitudinal axis and having a constant internal diameter, wherein the constant internal diameter of the third lumen section is not equal to the internal diameter of the first lumen section or any internal diameter of the tapered second lumen section.

15. The threaded enteral feeding coupling of claim 14, further comprising a body extension portion provided between the first end and the second end.

16. The threaded enteral feeding coupling of claim 14, further comprising a lumen extension tip projecting axially from within the cylindrical connection tip, the lumen extension tip being configured for fitting within an internal lumen of a male tip having a tapered lead-in portion, and being surrounded by a coaxial connection collar having an internally threaded annular surface comprising a coupling format that mates with and connects to the external threads of the cylindrical connection tip.

17. A method of coupling enteral connectors of different coupling formats together comprising:
providing a coupler comprising a first end and a second end, the first end substantially corresponding to an ISO 80369-3 compliant coupling format and the second end substantially conforming to a threaded enteral feeding coupling format, and an internal lumen extending through the coupling allowing fluid communication between the first end and the second end, wherein the internal lumen extends along a longitudinal axis, further wherein the internal lumen comprises a first lumen section at the first end having a constant internal diameter, a second lumen section at the second end having a tapered internal diameter, and a third lumen section disposed between the first lumen section and the second lumen section along the longitudinal axis and having a constant internal diameter, wherein the constant internal diameter of the third lumen section is not equal to the internal diameter of the first lumen section or any internal diameter of the tapered second lumen section;
providing a first connector substantially corresponding to an ISO 80369-3 compliant coupling;
providing a second connector substantially conforming to a threaded enteral feeding coupling format;
coupling the first connector to the first end of the coupling; and
coupling the second connector to the second end of the coupling.

18. The method of claim 17, further comprising delivery of an enteral fluid through the internal lumen between the first and second ends.

19. The threaded enteral feeding coupling of claim 14, further comprising a lumen extension tip projecting axially from within the cylindrical connection tip.

20. The enteral adaptor coupling of claim 1, wherein the internal diameter of the first lumen section is a constant diameter.

* * * * *